United States Patent
Habegger et al.

(10) Patent No.: US 8,758,354 B2
(45) Date of Patent: Jun. 24, 2014

(54) FLEXIBLE ATTACHMENT FOR AN EXTRAMEDULLARY SURGICAL INSTRUMENT

(75) Inventors: Abraham P. Habegger, Milford, IN (US); Jeffery A. VanDiepenbos, Syracuse, IN (US); Lindsay M. Hack, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 847 days.

(21) Appl. No.: 12/910,358

(22) Filed: Oct. 22, 2010

(65) Prior Publication Data

US 2012/0101504 A1    Apr. 26, 2012

(51) Int. Cl.
*A61B 17/60*    (2006.01)
*A61F 2/00*    (2006.01)

(52) U.S. Cl.
USPC ............................................................ 606/88

(58) Field of Classification Search
USPC ........................................ 606/86 R, 87–90
See application file for complete search history.

(56) References Cited

U.S. PATENT DOCUMENTS

| | | | |
|---|---|---|---|
| 5,445,640 A * | 8/1995 | Johnson et al. | 606/86 R |
| 5,628,750 A * | 5/1997 | Whitlock et al. | 606/88 |
| 6,053,922 A | 4/2000 | Krause et al. | |
| 6,554,837 B1 | 4/2003 | Hauri et al. | |
| 6,685,711 B2 | 2/2004 | Axelson, Jr. et al. | |
| 7,335,206 B2 | 2/2008 | Steffensmeier et al. | |
| 7,641,661 B2 | 1/2010 | Steffensmeier et al. | |
| 7,658,741 B2 | 2/2010 | Claypool et al. | |
| 2007/0173849 A1 | 7/2007 | Claypool et al. | |
| 2010/0222783 A1 | 9/2010 | May et al. | |

OTHER PUBLICATIONS

Sigma Classic Surgical Technique, DePuy Orthopaedics, Inc. 2010.
Zimmer NexGen Complete Knee Solution Extramedullary/Intramedullary Tibial Resector Surgical Technique, 2000, 2002, 2008 Zimmer, Inc.

* cited by examiner

*Primary Examiner* — Anu Ramana
(74) *Attorney, Agent, or Firm* — Schwegman Lundberg & Woessner, P.A.

(57) ABSTRACT

An extramedullary cut guide alignment assembly allows various adjustments to the cut guide without introducing bending stresses in the rest of the assembly. More particularly, the angular orientation of the cut guide with respect to the tibia may be freely changed during use, while maintaining the angular orientation of the proximal fixation arm of the alignment assembly with respect to the proximal tibial surface to which the arm is affixed. To achieve this decoupling of the angular orientations of the fixation arm and cut guide, the proximal fixation arm is pivotably mounted to the cut guide alignment assembly. Thus, the alignment assembly may be adjusted as necessary to achieve a desired angular orientation of the cut guide mounted thereto, while the pivotable junction between the alignment assembly and the proximal fixation arm automatically adjusts to accommodate the changing angular arrangement.

17 Claims, 5 Drawing Sheets

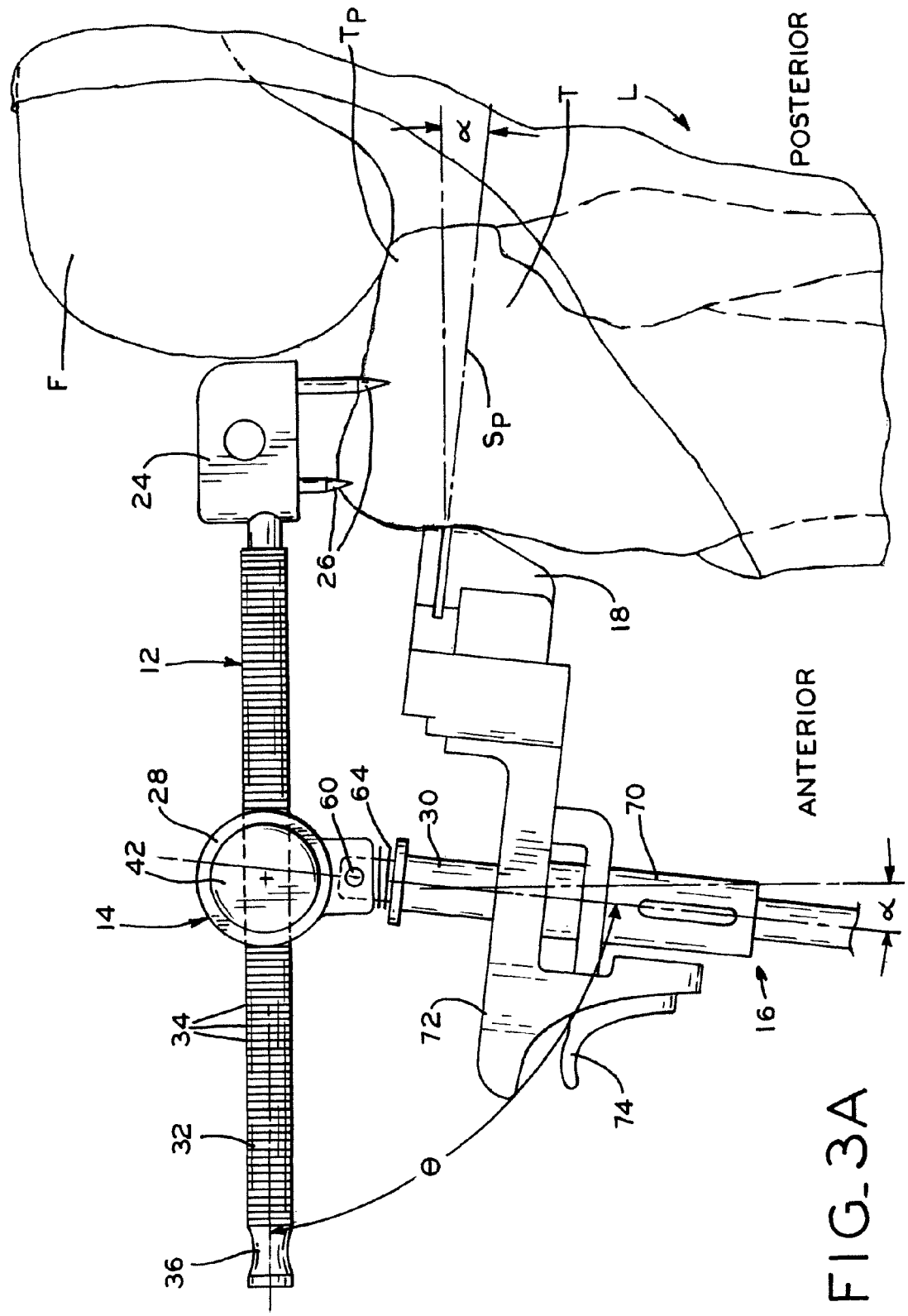
FIG_3A

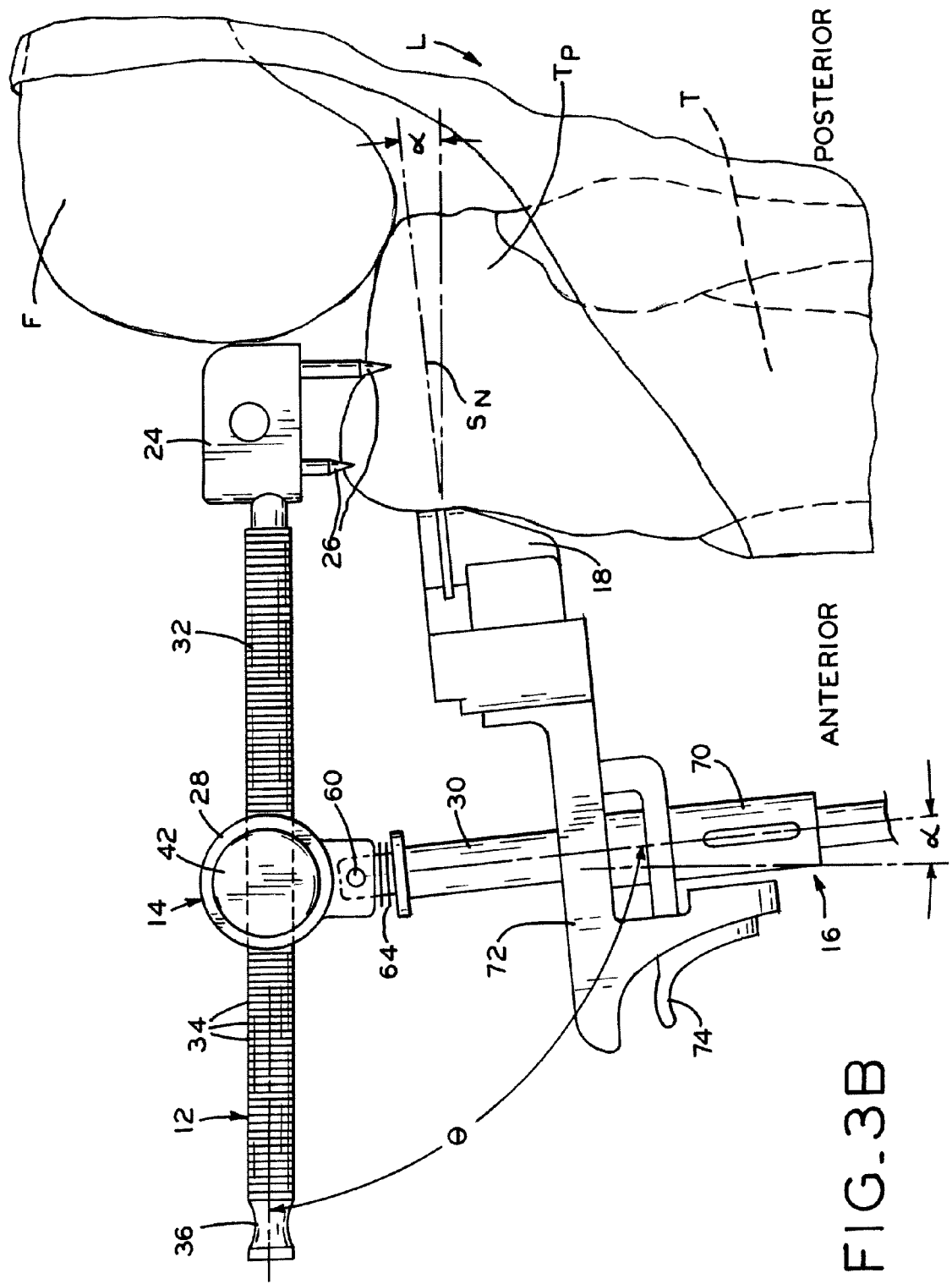
FIG._3B

FLEXIBLE ATTACHMENT FOR AN EXTRAMEDULLARY SURGICAL INSTRUMENT

BACKGROUND

1. Technical Field

The present disclosure relates to surgical instruments. More particularly, the present disclosure relates to extramedullary alignment devices for the alignment of cut guides used in knee arthroplasty.

2. Description of the Related Art

Orthopaedic prostheses are commonly utilized to repair and/or replace damaged bone and tissue in the human body. For example, knee arthroplasty procedures are used to implant a knee prosthesis including a femoral component, which may replace the articular surface of one or both of the natural femoral condyles and/or the natural femoral sulcus. The knee prosthesis may also include a tibial component which replaces the articular surface of the proximal end of the tibia with one or more components adapted to articulate with the femoral component.

Prior to installation of femoral or tibial components, the damaged and/or diseased portion of the natural tibia and/or femur is typically resected. These resections leave resected tibial and/or femoral surfaces, which then receive the prosthetic tibial and/or femoral components. The prosthetic components are typically designed to have particular geometrical arrangements relative to the surrounding anatomical structures, such as bones and ligaments, as well as to one another and any other prosthetic structures utilized in the surgery. To achieve a desired geometrical arrangement of a given prosthesis, the resected surface of the bone to which the prosthesis is mounted is typically subject to geometrical constraints of its own.

Substantial design efforts have focused on providing cut guides which aid in producing a particular resected surface adapted to receive a particular implant or set of implants. In addition, design efforts have focused on providing intraoperative flexibility to the surgeon performing the implantation procedure, to aid the surgeon in making adjustments or modifications to the surgical procedure according to his or her judgment, and in view of the unique circumstances in each individual case.

For resection of the tibia in knee arthroplasty, a cut guide is typically used to remove the proximal articular surface of the natural tibia in preparation for implantation of a prosthetic tibial component adapted to articulate with either the natural femur or a prosthetic femoral component. Such tibial cut guides are typically placed in a fixed position relative to the tibia using either an "extramedullary" cut guide fixation system or, alternatively, an "intramedullary" cut guide fixation system.

Intramedullary cut guide alignment instruments generally include a portion extending into the medullary canal of the tibia, with a cut guide coupled to the intramedullary portion and, thus, indexed to the proximal tibia.

Extramedullary fixation systems, on the other hand, are disposed outside the medullary canal of the tibia, and may be indexed to the patient's ankle at one end and to the proximal tibia surface at the other end. Components of one exemplary extramedullary cut guide alignment system are shown in U.S. Design patent application No. 29/362,749, now issued as U.S. Pat. No. D646,395, filed May 28, 2010 and entitled "ANKLE CLAMP," U.S. Design patent application No. 29/362,750, now issued as U.S. Pat. No. D651,313, filed May 28, 2010 and entitled "EXTRAMEDULLARY TELESCOPING TUBE AND ROD," U.S. Design patent application No. 29/362,752, now issued as U.S. Pat. No. D651,314, filed May 28, 2010 and entitled "EXTRAMEDULLARY MODULAR SPIKE ARM AND POST," and U.S. Design patent application No. 29/362,753, now issued as U.S. Pat. No. D646,388, filed May 28, 2010 and entitled "EXTRAMEDULLARY ROD ALIGNMENT ADAPTER," each of which is commonly assigned with the present application, the entire disclosures of which are hereby expressly incorporated by reference herein.

SUMMARY

The present disclosure provides an extramedullary cut guide alignment assembly in which various adjustments to the cut guide may be made without introducing bending stresses in the rest of the assembly. More particularly, the angular orientation of the cut guide with respect to the tibia may be freely changed during use, while maintaining the angular orientation of the proximal fixation arm of the alignment assembly with respect to the proximal tibial surface to which the arm is affixed. To achieve this decoupling of the angular orientations of the fixation arm and cut guide, the proximal fixation arm is pivotably mounted to the cut guide alignment assembly. Thus, the alignment assembly may be adjusted as necessary to achieve a desired angular orientation of the cut guide mounted thereto, while the pivotable junction between the alignment assembly and the proximal fixation arm automatically adjusts to accommodate the changing angular arrangement.

Advantageously, spikes formed in the head of the proximal fixation arm, which are partially driven into the tibia to affix the proximal fixation arm through the tibia, are not forced deeper into the tibia during the adjustment process. In the absence of this additional force, which may arise from adjusting the angle of the extramedullary cut guide, bending stresses which might otherwise accumulate in the cut guide alignment assembly are avoided.

In one form thereof, the present invention provides an instrument for aligning a cut guide in a particular angular arrangement with respect to a bone, the bone extending between a distal end and a proximal end, the instrument comprising: a body having a proximal body end, a distal body end and a body longitudinal axis, the distal body end adapted to be fixed to the distal end of the bone; a coupling head pivotably coupled to the proximal body end, the coupling head pivotable about a pivot axis; a fixation arm comprising: a fixation head adapted to be fixed to the proximal end of the bone; and a fixation shaft extending from the fixation head, the fixation shaft slidably coupled to the coupling head, such that the fixation arm is pivotable with respect to the body; and a cut guide coupled to the body, the cut guide defining a fixed angular orientation with respect to the body, the cut guide defining a variable angular orientation with respect to the fixation arm.

In another form thereof, the present invention provides an instrument for aligning a cut guide in a particular angular arrangement with respect to a bone, the bone extending between a distal end and a proximal end, the instrument comprising: a distal fixation assembly comprising: an ankle clamp adapted to be fixed to the bone proximate the distal end of the bone; and a distal shaft pivotably coupled to the ankle clamp for pivoting about a distal pivot axis, the shaft extending away from the ankle clamp; a body having a proximal body end, a distal body end and a body longitudinal axis, the distal body end selectively slidably coupled to the distal shaft, such that the body is pivotable with respect to the ankle clamp about the distal pivot axis; a coupling head pivotably coupled to the proximal body end for pivoting about a proximal pivot axis; a fixation arm comprising: a fixation head adapted to be fixed to the proximal end of the bone; and a fixation shaft extending from the fixation head, the fixation shaft slidably coupled to the coupling head, such that the fixation arm is pivotable with respect to the body; and a cut guide coupled to the body, the cut guide defining a fixed angular orientation with respect to the body, the cut guide defining a variable angular orientation with respect to the fixation arm.

In yet another form thereof, the present invention provides a method of resecting a tibia having a proximal end and a distal end, the method comprising: affixing an extramedullary cut guide assembly to the tibia, the extramedullary cut guide comprising: a body extending from the distal end of the tibia to the proximal end of the tibia; a spike arm pivotably connected to the body proximate the proximal end of the tibia; a distal fixation assembly coupled to the body proximate the distal end of the tibia; and a cut guide coupled to the body; affixing the spike arm to the proximal end of the tibia to define a spike arm angular orientation with respect to the tibia; affixing the distal fixation assembly to the tibia proximate the distal end of the tibia; adjusting a cut guide angular orientation with respect to the tibia, the step of adjusting the cut guide comprising: moving the body with respect to at least one of the distal fixation assembly and the spike arm; and during the step of moving the body, automatically pivoting the spike arm with respect to the body to maintain the spike arm angular orientation with respect to the tibia; and resecting the tibia using the cut guide.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 3A is a partial, side elevation view of a portion of the cut guide alignment assembly shown in FIG. 2, with a cut guide shown in a first angular orientation;

FIG. 3B is a partial, side elevation view of a portion of the cut guide alignment assembly shown in FIG. 2, with a cut guide shown in a second angular orientation;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

Figure 1:
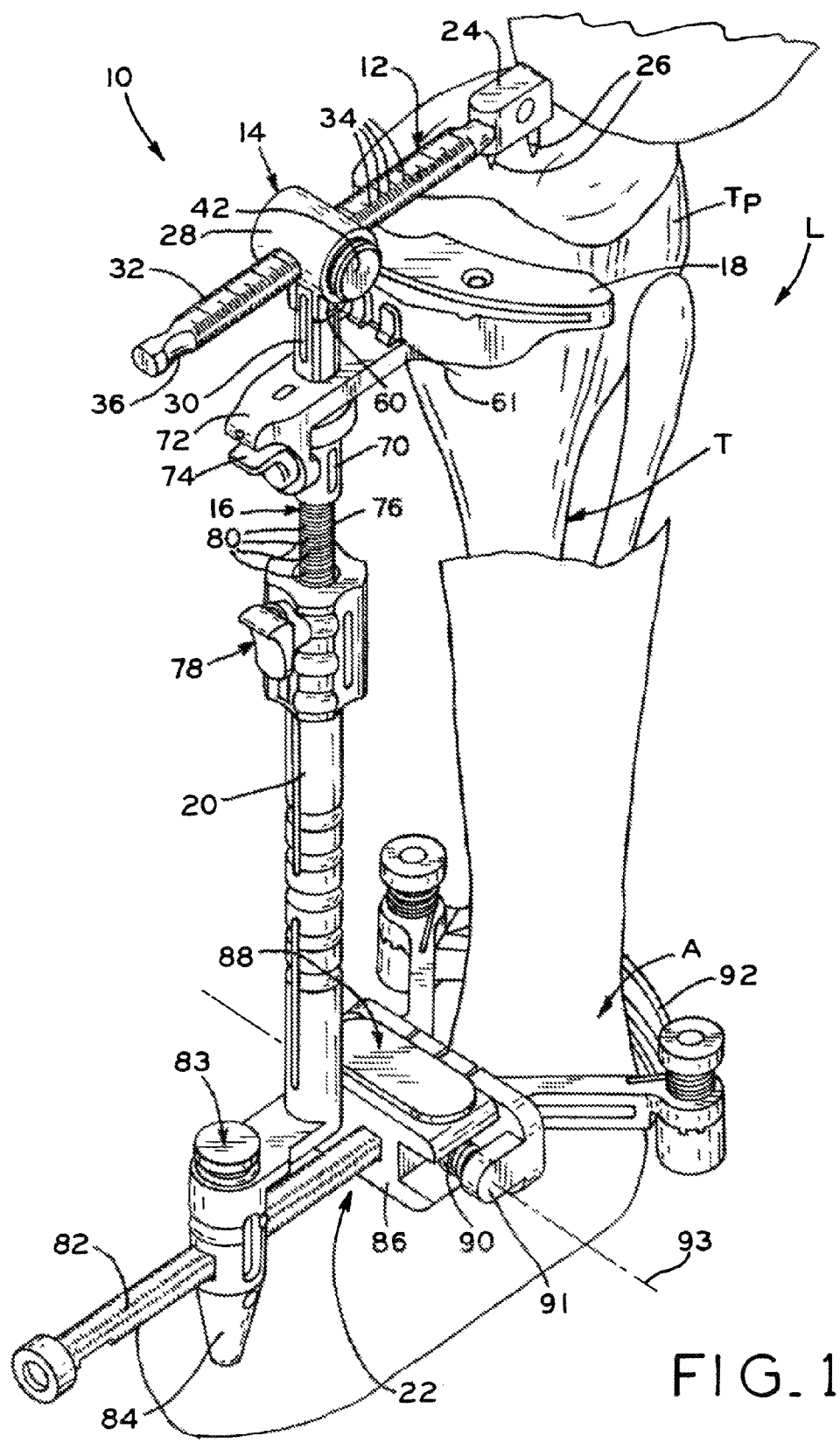
FIG. 1 is a perspective view of an extramedullary cut guide alignment assembly in accordance with the present disclosure, shown with the alignment assembly connected to the leg of a patient.

Referring now to FIG. 1, extramedullary cut guide alignment assembly 10 is shown fixed to leg L of a patient during a knee arthroplasty procedure. Cut guide alignment assembly 10 includes proximal fixation arm 12, which is fixed to proximal end $T_P$ of tibia T via head 24 having spikes 26. Fixation arm 12 is selectively slidably coupled to flexible coupling assembly 14, which includes coupling head 28 pivotably attached to coupling shaft 30, as described in detail below. Cut guide alignment assembly 10 further includes intermediate alignment rod 16, which is freely slidably coupled to coupling shaft 30 of coupling assembly 14, and is releasably slidably coupled to distal alignment tube 20. Cut guide 18 is releasably fixed to intermediate alignment rod 16. Distal fixation assembly 22, which is releasably slidably coupled to distal alignment tube 20, is shown affixed to ankle A of leg L, proximate the distal end (not shown) of tibia T. As described in detail below, the pivoted connection between coupling head 28 and coupling shaft 30 of flexible coupling assembly 14 allows a surgeon to change the angular orientation of cut guide 18 with respect to tibia T, while substantially maintaining the angular orientation of proximal fixation arm 12 with respect to tibia T.

As noted above, cut guide alignment assembly 10 includes several parts which are slidable with respect to one another. These slidable parts facilitate the use of cut guide alignment assembly 10 with a variety of different patients having different leg sizes and configurations. One exemplary cut guide assembly which may be adapted for use with a flexible coupling assembly in accordance with the present disclosure is disclosed in U.S. patent application Ser. No. 11/456,303, now issued as U.S. Pat. No. 7,842,039, filed Jul. 10, 2006, which is entitled METHOD AND APPARATUS FOR ACHIEVING CORRECT LIMB ALIGNMENT IN UNICONDYLAR KNEE ARTHROPLASTY and is commonly assigned with the present application, the entire disclosure of which is hereby expressly incorporated by reference herein. Another exemplary device and method of use relating to extramedullary resection devices is disclosed in a surgical technique brochure entitled "Zimmer® NexGen® Complete Knee Solution Extramedullary/Intramedullary Tibial Resector" (Zimmer® and NexGen® are registered trademarks of Zimmer, Inc. of 345 E. Main Street, Warsaw, Ind.), published by Zimmer, Inc. and having copyright dates in 2000, 2002 and 2008 (the "Zimmer Surgical Technique"), the entire disclosure of which is hereby expressly incorporated by reference herein.

Moreover, while the exemplary embodiment described herein advantageously allows for such adjustment, both intraoperatively for a given patient and among different patients, it is contemplated that much of the adjustability of cut guide alignment assembly 10 may be removed within the scope of the present disclosure.

For example, a simplified cut guide adjustment assembly may only include fixation arm 12, flexible coupling assembly 14 and ankle clamp 92 (described below). Shaft 30 of coupling assembly 14 may have a distal end slidably coupled to ankle clamp 92 for relative sliding of the distal end of shaft 30 toward or away from ankle clamp 92. A proximal end of shaft 30 is coupled to head 28 of coupling assembly 14. Head 28 may, in turn, be coupled to fixation arm 12, and cut guide 18 may be coupled directly to shaft 30. This simplified embodiment still allows cut guide 18 to be moved between different angular orientations while substantially maintaining fixation arm 12 in its original angular orientation in a similar manner as described below. A pivotal connection between ankle clamp 92 and shaft 30 will facilitate retaining fixation arm 12 in its original angular orientation while moving cut guide 18 to a different angular orientation, as further described herein below.

Moreover, various parts may be said to make up the body of cut guide alignment assembly 10. In the illustrated embodiment described below, flexible coupling assembly 14, intermediate alignment rod 16 and distal alignment tube 20 make up the body of assembly 10, in that these three parts span tibia T and link the fixed points established by fixation arm 12 and distal fixation assembly 22. However, it is contemplated that the body of alignment assembly 10 may be any combination of parts, or a single part, which spans this distance and links the fixed points established during the use of assembly 10 (as described in detail below).

Whether the body of cut guide alignment assembly 10 is constructed of multiple components or a single component, the body defines longitudinal axis 11 (FIG. 2) extending proximally-distally. Longitudinal axis 11 is generally aligned with anatomic axis $T_A$ of tibia T when assembly 10 is mounted to tibia T.

Figure 2:
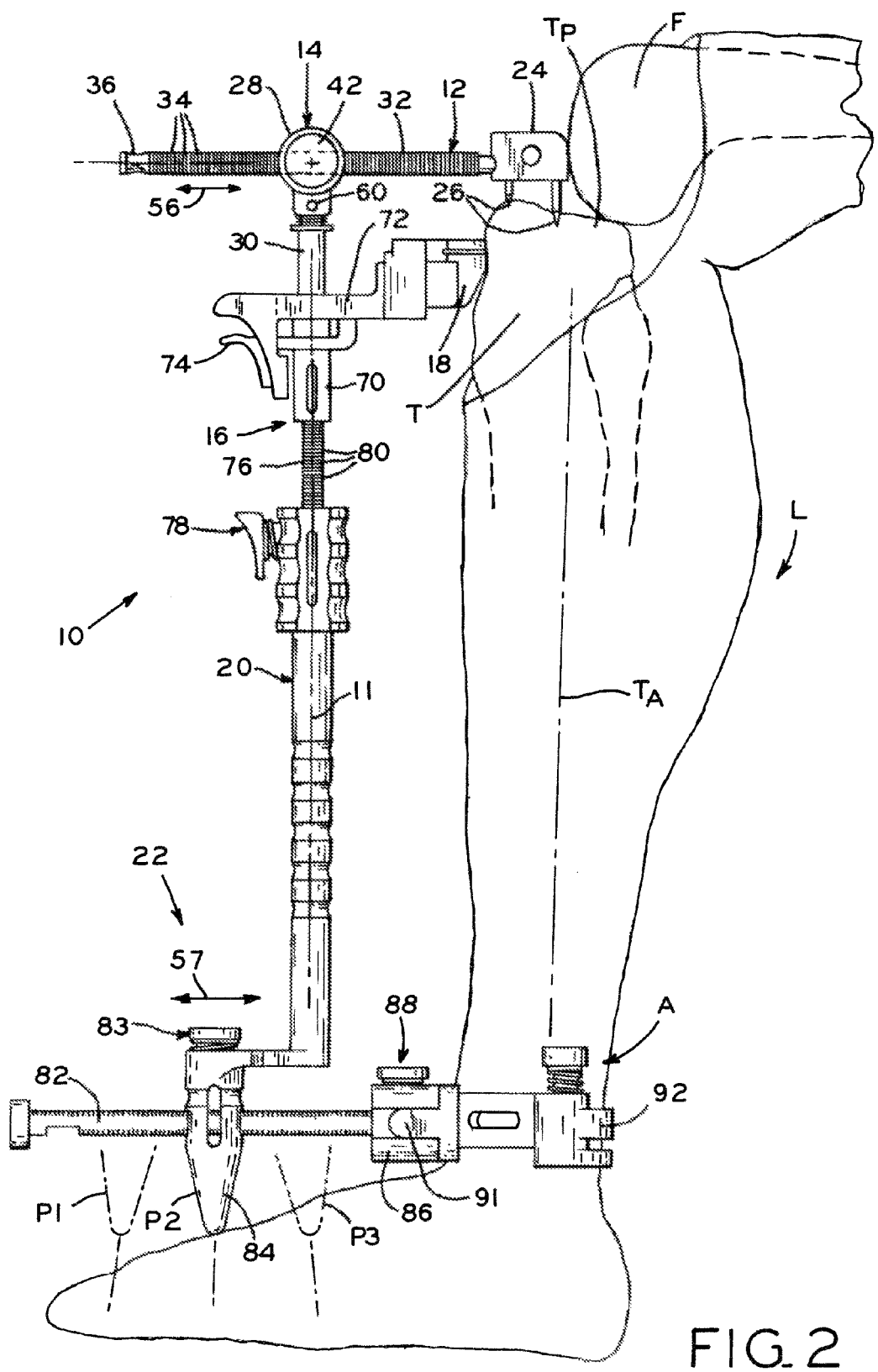
FIG. 2 is a side, elevation view of the extramedullary cut guide alignment assembly shown in FIG. 1.

Referring now to FIGS. 1 and 2, fixation arm 12 includes head 24 having spikes 26 extending distally therefrom. As best seen in FIG. 2, spikes 26 may have varying lengths to accommodate natural variation in the articular surface at proximal end $T_P$ of natural tibia T. Extending generally anteriorly from fixation head 24 is fixation arm shaft 32, which has a plurality of annular ridges 34 disposed along the extent thereof for mating engagement with coupling head 28 of coupling assembly 14 as described below. Fixation arm shaft 32 may further include gripping portion 36 to facilitate manipulation of fixation arm 12 with respect to the remainder of alignment assembly 10.

Figure 4:
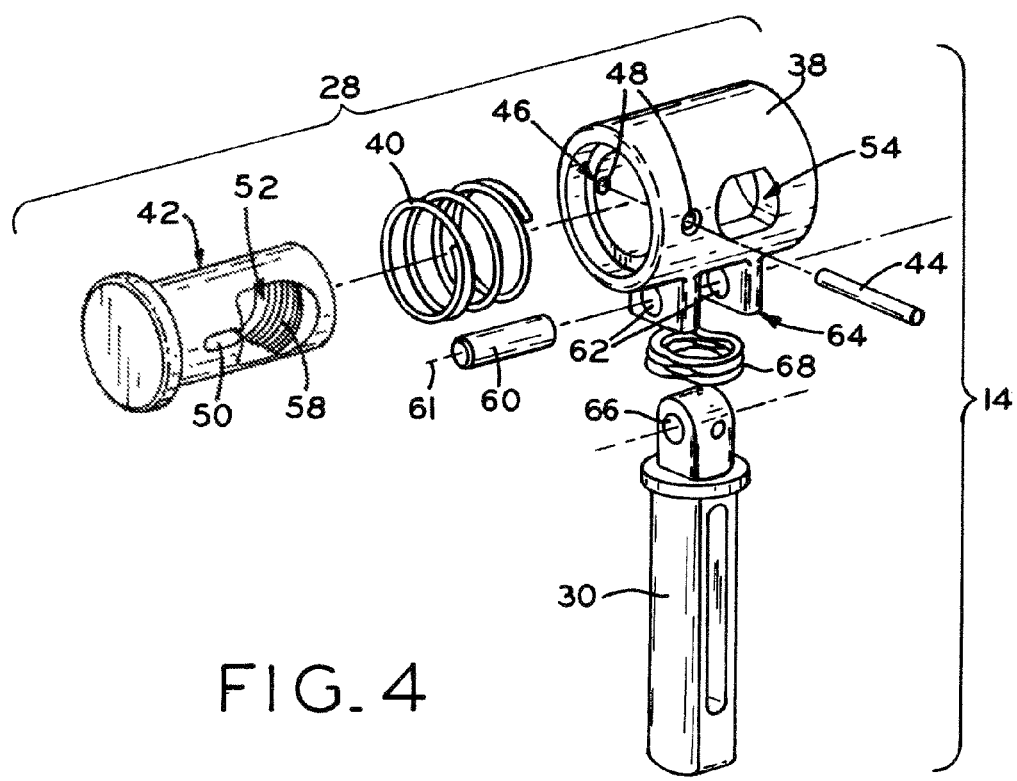
FIG. 4 is a perspective, exploded view of a flexible coupling assembly in accordance with the present disclosure.

Flexible coupling assembly 14 includes coupling head 28 pivotally attached to coupling shaft 30. As best seen in FIG. 4, coupling head 28 includes housing 38, spring 40, actuator 42 and retention pin 44. Spring 40 and actuator 42 are received within cavity 46 of housing 38, with spring 40 biasing actuator 42 outwardly. Actuator 42 is retained within cavity 46 against the biasing force of spring 40 by retention pin 44, which passes through apertures 48 formed in housing 38 and slot 50 formed in actuator 42. Slot 50 allows actuator 42 to be pushed further into cavity 46 of housing 38 against the biasing force of spring 40, such that aperture 52 of actuator 42 aligns with apertures 54 formed in opposing sides of housing 38 when actuator 42 is pushed sufficiently far into cavity 46. When apertures 52, 54 are aligned in this way, fixation arm shaft 32 is freely movable along direction 56 (FIG. 2) and can be received in or removed from head 28 (FIG. 2). Once shaft 32 is deemed to be properly positioned within head 28, actuator 42 is released to allow the biasing force of spring 40 to urge engagement between annular ridges 58 formed in the wall defining aperture 52 of actuator 42 and annular ridges 34 formed on fixation arm shaft 32. When so engaged, annular ridges 34, 58 prevent any further sliding of fixation arm 12 with respect to flexible coupling assembly 14.

Coupling head 28 is pivotably coupled to coupling shaft 30 via pivot pin 60, which defines pivot pin axis 61 (FIGS. 1 and 4). As shown in FIG. 4, pivot pin 60 is received within apertures 62 formed in stanchion 64 of housing 38. Pivot pin 60 also passes through aperture 66 formed in shaft 30 to pivotably couple head 28 to shaft 30. Leaf spring 68 is disposed between head 28 and shaft 30, creating a biasing force against rotation of head 28 about pivot pin 60. As described in detail below, application of force to spikes 26 of fixation arm 12 will tend to rotate head 28 with respect to coupling shaft 30 against the biasing force of leaf spring 68.

Pivot pin axis 61 is oblique to longitudinal axis 11 of the body of cut guide alignment assembly 10. In an exemplary embodiment, pivot pin axis 61 is generally perpendicular to longitudinal axis 11. In addition, pivot pin axis 61 is substantially parallel to lateral shaft axis 93 of lateral shaft 90 (FIG. 1), which is described in detail below.

Shaft 30 of flexible coupling assembly 14 is freely slidably received within proximal portion 70 of intermediate shaft 16. More particularly, proximal portion 70 is cannulated to receive shaft 30 of coupling assembly 14, as shown in FIG. 2. Cut guide 18 is coupled to intermediate shaft 16 in a fixed angular orientation by any suitable method or structure. For example, cut guide 18 may be bolted, welded or otherwise permanently affixed to intermediate shaft 16. Where cut guide is permanently affixed, a plurality of different intermediate shafts 16 may be provided for selecting among different cut guides for use in cut guide alignment assembly 10. In an exemplary embodiment, cut guide 18 may be releasably attached to intermediate shaft 16, such as by a dovetail attachment (as shown in the Zimmer Surgical Technique, incorporated by reference above) or a releasable threaded attachment (such as a thumbscrew), for example. In the exemplary embodiment of FIG. 2, proximal portion 70 of intermediate shaft 16 includes cut guide mounting assembly 72 for releasably coupling cut guide 18 to intermediate alignment rod 16 in a fixed angular orientation. Handle 74 is provided for releasing cut guide 18 from cut guide mounting assembly 72.

Cut guide 18 is shown and described herein as being attached to intermediate shaft 16, which advantageously allows cut guide 18 to be vertically adjusted with respect to the fixed proximal and distal points established by fixation arm 12 and distal fixation assembly 22, respectively. As described in detail below, the vertical adjustment is accomplished by sliding distal portion 76 into or out of distal alignment tube 20. As this sliding occurs, coupling shaft 30 slides into or out of cannulated proximal portion 70 of intermediate shaft 16, thereby allowing cut guide 18 to be vertically adjusted without disturbing the fixed points established by ankle clamp 92 and fixation arm 12. However, it is contemplated that cut guide 18 may be coupled to the other components of cut guide alignment assembly 10 by any suitable structure or method.

Distal portion 76 of intermediate alignment rod 16 is received within distal alignment tube 20. Distal alignment tube 20 includes coupling and release mechanism 78 adapted to cooperate with annular ridges 80 (FIG. 2) formed on distal portion 76 of rod 16 in a similar fashion to the above-described releasably slidable coupling mechanism used for locking fixation arm 12 to coupling head 28 of flexible coupling assembly 14 (the coupling mechanism comprising ridges 34, 52 formed on shaft 32 and actuator 42, respectively). Similarly, a third coupling/releasing mechanism 83 releasably slidably couples distal extension 84 of distal alignment tube 20 with ridged shaft 82 of distal fixation assembly 22.

Referring to FIG. 1, distal fixation assembly 22 includes shaft 82 fixed to lateral adjustment block 86. Received within lateral adjustment block 86 is a fourth coupling/releasing mechanism 88 which engages a ridged lateral shaft 90 passing through adjustment block 86, such that shaft 90 is substantially perpendicular to both shaft 82 and distal alignment tube 20. Ankle clamp 92 is fixed to lateral shaft 90 via shaft mount 91. Limited pivotable rotation between ankle clamp 92 and adjustment block 86 is permitted, because adjustment block 86 is rotatable about axis 93 of lateral shaft 90. Thus, ultimately, limited pivotable rotation is allowed between ankle clamp 92 and cut guide 18 about axis 93 of shaft 90. Ankle clamp 92 operates to affix the distal end of cut guide arm and assembly 10 to leg L (FIG. 1) around ankle A near the distal end of tibia T.

In use, cut guide assembly 10 allows a surgeon to align cut guide 18 in a particular desired angular orientation with respect to proximal end $T_P$ of tibia T, while preventing any buildup of bending force or stress in the other components of cut guide alignment assembly 10 that might otherwise arise in an extramedullary guide assembly with a fixation arm rigidly connected to the body of the guide when the angular orientation of the fixation arm is changed with respect to tibia T. In the embodiment illustrated in FIG. 1, flexible coupling assembly 14 allows the change in angular orientation to avoid this stress or force buildup, as described below. However, other embodiments are contemplated which can achieve similarly advantageous results, as also discussed below.

Prior to affixing extramedullary cut guide alignment assembly 10 to leg L, the patient may be prepared and the tissue around the knee joint may be retracted in accordance with conventional surgical procedures. Femur F may be placed in a flexion orientation with respect to tibia T, as shown in FIG. 2, and other anatomical structures may be retracted or resected as necessary to expose the proximal articular surface at proximal end $T_P$ of tibia T. With the proximal surface of tibia T exposed, cut guide alignment assembly 10 is ready to be attached to leg L and utilized as described below.

Ankle clamp 92 is affixed to ankle A of leg L to couple distal fixation assembly 22 to leg L. One exemplary ankle clamp useable with the present invention is disclosed in U.S. patent application Ser. No. 11/456,303, now issued as U.S. Pat. No. 7,842,039, entitled METHOD AND APPARATUS FOR ACHIEVING CORRECT LIMB ALIGNMENT IN UNICONDYLAR KNEE ARTHROPLASTY, incorporated by reference above. Using ankle clamp 92, distal fixation assembly 22 represents a fixed point relative to the distal end of tibia T. Intermediate alignment rod 16 and/or coupling shaft 30 are then adjusted as necessary to move spikes 26 of fixation arm 12 into contact with the proximal tibial surface, and spikes 26 are partially driven into proximal tibial end $T_P$ to fix head 24 of fixation arm 12 to tibia T. Thus, fixation arm 12 represents a fixed point relative to proximal end $T_P$ of tibia T. In an extramedullary cut guide assembly having a spike arm rigidly connected to the body of the extramedullary cut guide, having fixed points of attachment to the tibia results in the longitudinal axis of the body (which may be a nested, telescoping arrangement, for example) typically being aligned to the leg of the patient. With flexible coupling assembly 14, on the other hand, longitudinal axis 11 of the body of assembly 10 can be moved out of alignment with leg L without introduction of bending stresses in the body, as discussed below.

With the fixed end points of cut guide assembly 10 now set, cut guide 18 may be selected and mounted to proximal potion 70 of intermediate alignment rod 16. Cut guide 18 is then positioned at an appropriate height with respect to tibia T, depending on the amount of tibia T to be resected and surgeon preference. In the exemplary embodiment illustrated in FIGS. 1 and 2, positioning of cut guide 18 and the adjustment of cut guide assembly 10 are facilitated by the nested, telescoping arrangement of components forming the body of cut guide assembly 10. To adjust the height of cut guide 18, release mechanism 78 is actuated to release intermediate rod 16 from distal alignment tube 20, and is slidably moved vertically as shaft 30 slides freely within proximal portion 70 of shaft 16. Shaft 30 is long enough to remain engaged in the cannulated proximal portion 70 of shaft 16 even if cut guide 18 is adjusted to a lowest position (i.e., adjacent to distal alignment tube 20). When a proper height for cut guide 18 has been achieved, coupling/releasing mechanism 78 is reengaged to slidably fix intermediate alignment rod 16 with respect to distal alignment tube 20.

At this point in the surgical procedure, cut guide assembly 10 is fixed at both ends of tibia T and cut guide 18 is at the desired vertical height. In addition to height adjustment, a surgeon may also wish to define the "tibial slope" that will result from making a cut through cut guide 18. For example, the surgeon may wish to perform a resection resulting in positive tibial slope $S_P$, as shown in FIG. 3A, in which the resected tibial surface slopes proximally from posterior to anterior. Alternatively, the surgeon may instead opt for negative tibial slope $S_N$, as shown in FIG. 3B, in which the resected tibial surface slopes distally from posterior to anterior. The choice between a positive and negative tibial slope, and the amount or angle of positive or negative slope, may depend upon a variety of factors, such as correction of deformities, matching of the native slope of the preoperative tibia, accommodation of a particular tibial prosthesis, and the like.

To achieve a positive tibial slope as shown in FIG. 3A, a surgeon may vary the angular orientation of cut guide 18 with respect to tibia T by sliding distal extension 84 away from leg L along direction 57 (FIG. 2). In the exemplary embodiment shown in FIG. 2, this is accomplished by actuating distal coupling/releasing mechanism 83 to decouple distal alignment tube 20 from distal fixation assembly 22, sliding distal extension 84 along shaft 82 from central position P2 to distant position P1, and releasing mechanism 83 to lock cut guide alignment assembly 10 in the new configuration.

Alternatively or in addition to moving distal extension 84, the surgeon may reorient cut guide 18 into a positive-slope angular orientation by actuating actuator 42 of flexible coupling assembly 14 to decouple coupling assembly 14 from fixation arm 12, sliding coupling assembly 14 toward leg L along direction 56, and releasing actuator 42 to reengage coupling assembly 14 with fixation arm 12. Either way, varying the angular orientation of cut guide 18 with respect to tibia T also changes angle θ formed between coupling shaft 30 and fixation arm shaft 32 (FIG. 3A). The magnitude of this change is represented by angle α, which is equal to the amount of change in the tibial slope.

Adjusting cut guide alignment assembly 10 to produce negative slope $S_N$ is accomplished by a similar process, except distal extension is moved closer to leg L, i.e., from central position P2 to near position P3 (FIG. 2) and/or sliding coupling assembly 14 away from leg L along direction 56. In the illustrated embodiment of FIG. 3B, cut guide 18 has been adjusted to produce negative slope $S_N$ having angle α, though of course any angle may be chosen. In addition, cut guide 18 may itself have a particular "base" slope angle, either positive or negative, which can be adjusted in the manner described above.

The change in angle θ resulting from adjustment of slope angles $S_P$, $S_N$ operates to pivot coupling shaft 30 with respect to coupling head 28 against the biasing force of leaf spring 68. Advantageously, this angular change permitted by flexible coupling assembly 14 allows fixation arm 12 to remain in the same angular orientation with respect to tibia T as was present prior to the change in angular orientation of cut guide 18, as shown in FIGS. 3A and 3B. Further, bending forces placed on coupling shaft 30 by the adjustment of angle θ are minimized, thereby reducing the friction created by adjustment of intermediate shaft 16, distal alignment tube 20 and/or coupling shaft 30. Advantageously, this reduced friction ensures that intraoperative adjustments of assembly 10 are smooth, precise and easy. Further, bending forces transmitted to tibia T via fixation arm 12 and/or distal fixation assembly 22 are also minimized, thereby ensuring an accurate and efficient resection of same.

To accommodate the pivoting movement of coupling head 28 with respect to shaft 30, which occurs at the proximal portion of cut guide assembly 10, pivoting motion of shaft 82 with respect to ankle clamp 92 also occurs at the distal portion of cut guide assembly 10. Referring to FIG. 1, shaft 82 and lateral adjustment block 86 are pivotable about axis 93 of lateral shaft 90, which is oblique to longitudinal axis 11. In order to maintain the orientation of fixation arm 12 with respect to tibia T, shaft 82 pivots proximally or distally as distal extension 84 of distal alignment tube is adjusted to a new position (i.e., positions P1 or P3 shown in FIG. 2) along shaft 82.

Once the surgeon is satisfied with the definition of tibial slope $S_P$ or $S_N$, the surgeon uses cut guide 18 to resect tibia T in accordance with conventional resection procedures.

In an exemplary embodiment, the total angular range of cut guide assembly 10, i.e., the angular sweep between angle α for a maximum negative tibial slope $S_N$ and angle α for a maximum positive tibial slope $S_P$ (FIGS. 3A and 3B), may be up to 20° or more. More particularly, flexible coupling assembly 14 may allow a positive slope $S_P$ as large as 7°, 9° or 12°, for example, and a negative slope $S_N$ as large as 5°, 7° or 8°, or slopes $S_P$, $S_N$ may be any slope within any range defined by the forgoing values.

Figure 5:
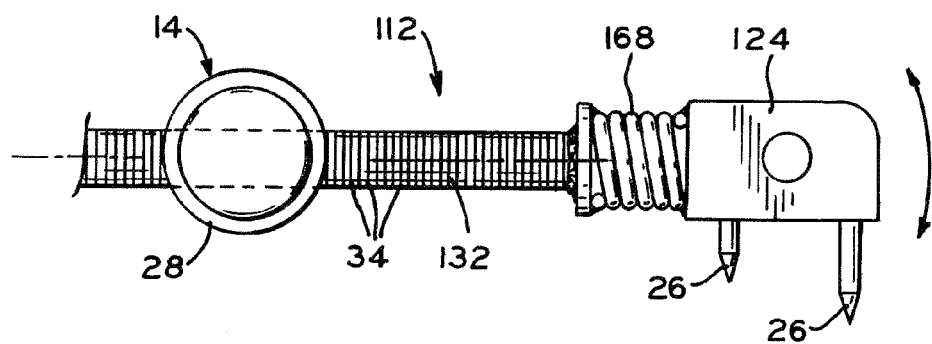
FIG. 5 is a side, elevation view of a flexible fixation arm in accordance with the present disclosure.

Referring now to FIG. 5, flexible coupling assembly 14 may be replaced by, or augmented with, flexible fixation arm 112. Flexible fixation arm 112 may have fixation head 124 and fixation arm shaft 132, similar to fixation head 24 and fixation shaft 32 described above. However, tension spring 168 may be used to connect head 124 and shaft 132, thereby allowing fixation head 124 to bend with respect to fixation shaft 132 in any direction. Advantageously, the multi-direction movement of flexible fixation arm 112 allows head 124 to move in a first pivot direction to accommodate positive and negative tibial slopes $S_P$, $S_N$ as described above, but also allows movement in other, different pivot directions, such as to accommodate, e.g., a varus/valgus slope for resection of tibia T.

Similarly, a second axis of rotation can be introduced to flexible coupling assembly 14, with the second axis normal or oblique to axis 61 of pivot pin 60 in the manner of a mechanical U-joint. This second axis of rotation would also allow a varus/valgus adjustment of the cut plane applied to tibia T by cut guide 18.

In yet another alternative embodiment, all or a portion of fixation shafts 32, 132 and/or coupling shaft 30 of flexible coupling assembly 14 may themselves be flexible. For example, shafts 32, 132 and/or 30 may be made of a flexible material such as rubber, polymer, or the like. In one exemplary embodiment, the flexible shaft may be made in accordance with U.S. Pat. No. 6,053,922, filed Jul. 17, 1996 and entitled "FLEXIBLE SHAFT," the entire disclosure of which is hereby expressly incorporated by reference herein.

While this invention has been described as having exemplary designs, the present disclosure can be further modified within the spirit and scope of this invention. This application is therefore intended to cover any variations, uses, or adaptations of the invention using its general principles. Further, this application is intended to cover such departures from the present disclosure as come within known or customary practice in the art to which this invention pertains and which fall within the scope of the appended claims.

What is claimed is:

1. An instrument for aligning a cut guide in a particular angular arrangement with respect to a bone, the bone extending between a distal end and a proximal end, the instrument comprising:

a body having a proximal body end, a distal body end and a body longitudinal axis, the distal body end adapted to be fixed to the distal end of the bone, the body including a coupling shaft;

a coupling head pivotably coupled to the coupling shaft, the coupling head pivotable about a pivot axis;

a spring disposed between the coupling head and the coupling shaft, the spring biasing the coupling head against rotation with respect to the coupling shaft;

a fixation arm comprising:
  a fixation head adapted to be fixed to the proximal end of the bone; and
  a fixation shaft extending from the fixation head, the fixation shaft slidably coupled to the coupling head, such that the fixation arm is pivotable with respect to the body; and a cut guide coupled to the body, the cut guide defining a fixed angular orientation with respect to the body, the cut guide defining a variable angular orientation with respect to the fixation arm.

2. The instrument of claim 1, wherein the bone defines an anatomic axis, wherein the cut guide defines an anterior/posterior slope angle relative to the anatomic axis and wherein the pivot axis is oblique to the anatomic axis when the body longitudinal axis is aligned with the anatomic axis, whereby rotation of the coupling head relative to the body about the pivot axis effects adjustment of the anterior/posterior slope angle of the cut guide.

3. The instrument of claim 2, wherein the cut guide defines a varus/valgus slope angle relative to the anatomic axis, wherein the coupling head is pivotably coupled to the proximal body end about a second pivot axis, wherein the second pivot axis is oblique to the first pivot axis and whereby rotation of the coupling head relative to the body about the second pivot axis effects adjustment of the varus/valgus slope angle of the cut guide.

4. The instrument of claim 1, wherein the bone defines an anatomic axis, wherein the cut guide defines a varus/valgus slope angle relative to the anatomic axis and wherein the pivot axis is one of coplanar and parallel to the anatomic axis when the body longitudinal axis is aligned with the anatomic axis, whereby rotation of the coupling head relative to the body about the pivot axis effects adjustment of the varus/valgus slope angle of the cut guide.

5. The instrument of claim 1, further comprising:
  a clamp adapted to be coupled to the distal end of the bone; and
  a distal fixation shaft extending from the clamp, the distal body end slidably coupled to the distal fixation shaft, whereby sliding the distal body end with respect to the clamp pivots the coupling head about the pivot axis and thereby changes the variable angular orientation of the cut guide with respect to the fixation arm.

6. The instrument of claim 1, wherein the body further comprises:
  an intermediate shaft slidably coupled to the coupling shaft, the cut guide coupled to the intermediate shaft; and
  a distal alignment tube slidably coupled to the intermediate shaft, the distal alignment tube adapted to be fixed to the distal end of the bone.

7. The instrument of claim 6, wherein the distal alignment tube includes a coupling/releasing mechanism operable to releasably slidably fix the intermediate shaft with respect to the distal alignment tube.

8. The instrument of claim 1, wherein the coupling head comprises:

a coupling head housing;

an actuator received within the coupling head housing, the actuator operable to engage the fixation shaft; and a coupling head spring disposed between the actuator and the coupling head housing, the coupling head spring biasing the actuator into engagement with the fixation shaft.

9. The instrument of claim 8, wherein the actuator includes a plurality of annular ridges, and the fixation shaft includes a plurality of complementary annular ridges, in which the annular ridges of the actuator and the annular ridges of the fixation shaft cooperate to releasably slidably lock the fixation shaft to the coupling head when the actuator engages the fixation shaft.

10. The instrument of claim 1, wherein the coupling head further comprises:

a coupling head housing including a stanchion; and a pivot pin at least partially received within the stanchion and an aperture of the coupling shaft so as to pivotably couple the coupling head to the coupling shaft.

11. An instrument for aligning a cut guide in a particular angular arrangement with respect to a bone, the bone extending between a distal end and a proximal end, the instrument comprising:

a distal fixation assembly comprising:

an ankle clamp adapted to be fixed to the bone proximate the distal end of the bone; and a distal shaft pivotably coupled to the ankle clamp for pivoting about a distal pivot axis, the shaft extending away from the ankle clamp;

a body having a proximal body end, a distal body end and a body longitudinal axis, the distal body end selectively slidably coupled to the distal shaft, such that the body is pivotable with respect to the ankle clamp about the distal pivot axis;

a coupling head pivotably coupled to the proximal body end for pivoting about a proximal pivot axis;

a flexible fixation arm comprising:

a fixation head adapted to be fixed to the proximal end of the bone; and a fixation shaft extending from the fixation head and coupled to the fixation head by a tension spring such that the fixation head is bendable with respect to the fixation shaft, the fixation shaft slidably coupled to the coupling head, such that the fixation arm is pivotable with respect to the body; and a cut guide coupled to the body, the cut guide defining a fixed angular orientation with respect to the body, the cut guide defining a variable angular orientation with respect to the fixation arm.

12. The instrument of claim 11, wherein the bone defines an anatomic axis, wherein the cut guide defines an anterior/posterior slope angle relative to the anatomic axis and wherein the proximal pivot axis and the distal pivot axis are oblique to the anatomic axis when the body longitudinal axis is aligned with the anatomic axis, whereby rotation of the body about at least one of the proximal pivot axis and the distal pivot axis effects adjustment of the anterior/posterior slope angle of the cut guide.

13. The instrument of claim 11, wherein the bone defines an anatomic axis, wherein the cut guide defines a varus/valgus slope angle relative to the anatomic axis, wherein the proximal pivot axis defines a first proximal pivot axis, the coupling head pivotably coupled to the proximal body end about a second proximal pivot axis that is oblique to the first proximal pivot axis, whereby rotation of the coupling head relative to the body about the second proximal pivot axis effects adjustment of the varus/valgus slope angle of the cut guide.

14. The instrument of claim 11, wherein the body further comprises:

a coupling shaft pivotally coupled to the coupling head; and a spring disposed between the coupling head and the coupling shaft, the spring biasing the coupling head against rotation with respect to the coupling shaft.

15. A method of resecting a tibia having a proximal end and a distal end, the method comprising:

affixing an extramedullary cut guide assembly to the tibia, the extramedullary cut guide comprising:

a body extending from the distal end of the tibia to the proximal end of the tibia, the body including a coupling shaft pivotably coupled to a coupling head;

a spike arm pivotably connected to the coupling head proximate the proximal end of the tibia, wherein a spring is disposed between the coupling head and the coupling shaft, the spring biasing the coupling head against rotation with respect to the coupling shaft;

a distal fixation assembly coupled to the body proximate the distal end of the tibia; and a cut guide coupled to the body;

affixing the spike arm to the proximal end of the tibia to define a spike arm angular orientation with respect to the tibia;

affixing the distal fixation assembly to the tibia proximate the distal end of the tibia;

adjusting a cut guide angular orientation with respect to the tibia, the step of adjusting the cut guide comprising:

moving the body with respect to at least one of the distal fixation assembly and the spike arm; and during the step of moving the body, automatically pivoting the spike arm with respect to the body to maintain the spike arm angular orientation with respect to the tibia; and resecting the tibia using the cut guide.

16. The method of claim 15, wherein the step of adjusting the cut guide comprises adjusting a tibial slope angle.

17. The method of claim 15, wherein the step of adjusting the cut guide comprises adjusting a varus/valgus angle.

* * * * *